US010316328B2

(12) United States Patent
Bachlava et al.

(10) Patent No.: US 10,316,328 B2
(45) Date of Patent: Jun. 11, 2019

(54) MELON PLANTS WITH IMPROVED TRAITS

(71) Applicant: SEMINIS VEGETABLE SEEDS, INC., St. Louis, MO (US)

(72) Inventors: Eleni Bachlava, Fairfield, CA (US); Alfonso Cuesta-Marcos, St. Louis, MO (US); Jeffrey M. Mills, Woodland, CA (US); Kelli M. Durham, St. Louis, MO (US); Robyn L. Morgan, St. Louis, MO (US); Tarek Joobeur, Sacramento, CA (US); Susana Garcia Andrés, Almeria (ES)

(73) Assignee: SEMINIS VEGETABLE SEEDS, INC., Woodland, CA (US)

( * ) Notice: Subject to any disclaimer, the term of this patent is extended or adjusted under 35 U.S.C. 154(b) by 0 days.

(21) Appl. No.: 15/675,544

(22) Filed: Aug. 11, 2017

(65) Prior Publication Data

US 2018/0094276 A1 Apr. 5, 2018

Related U.S. Application Data

(60) Provisional application No. 62/381,469, filed on Aug. 30, 2016.

(51) Int. Cl.
*A01H 5/08* (2018.01)
*C12N 15/82* (2006.01)
*A01H 1/02* (2006.01)

(52) U.S. Cl.
CPC .......... *C12N 15/8282* (2013.01); *A01H 1/02* (2013.01); *A01H 5/08* (2013.01); *C12N 15/82* (2013.01); *C12N 15/8283* (2013.01)

(58) Field of Classification Search
None
See application file for complete search history.

(56) References Cited

U.S. PATENT DOCUMENTS

| 8,962,931 | B2 | 2/2015 | Kassies et al. |
| 8,987,561 | B2 | 3/2015 | Collin et al. |
| 2015/0313107 | A1 | 11/2015 | Ogundiwin et al. |

FOREIGN PATENT DOCUMENTS

| WO | WO 2010/025747 A1 | 3/2010 |
| WO | WO 2012/116938 A1 | 9/2012 |
| WO | Wo 2015/150560 A1 | 10/2015 |

OTHER PUBLICATIONS

Bertrand et al., "AR Hale's Best Jumbo, a new differential melon variety for *Sphaerotheca fuliginea* races in leaf disk tests," *Cucurbitaceae*, 234-237, 2002.
Diaz et al., "A consensus linkage map for molecular markers and quantitative trait loci associated with economically important traits in melon (*Cucumis melo* L.)," *BMC Plant Biology*, 11:111, 2011.
Dogimont et al., "Molecular diversity at the Vat/Pm-W resistance locus in Melon," *Cucubitaceae 2008*, 219:277, 2008.
Dogimont et al., "The Vat locus encodes for a CC-NBS-LRR portein that confers resistance to *Aphis gossypii* infestation and *A. gossypii*-mediated virus resistance," *Plant J*, 80:993-1004, 2014.
Epinat et al., "Genetic analysis of resistance of five melon lines to powdery mildews," *Euphytica*, 65:135-144, 1993.
Fazza et al., "Mapping of resistance genes to races 1, 3 and 5 of *Podosphaera xanthii* in melon PI 414723," *Crop Breed Appl Biotechnol*, 13:349-355, 2013.
Fukino et al., "Identification of QTLs for resistance to powdery mildew and SSR markers diagnostic for powdery mildew resistance genes in melon (*Cucumis melo* L.)," *Theor Appl Genet*, 118:165-175, 2008.
International Search Report and Written Opinion for PCT/US2017/046574 dated Nov. 13, 2017.
Kuzuya et al., "Powdery mildew (*Podosphaera xanthii*) resistance in melon is categorized into two types based on inhibition of the infection processes," *J Exp Bot*, 57(9):2093-2100, 2006.
McCreight et al., "AR Hale's Best Jumbo, AR 5, and AR Topmark: melon aphid-resistant muskmelon breeding lines," *HortScience*, 19(2):309-310, 1984.
McCreight et al., "Inheritance of resistance in melon PI 313970 to cucurbit powdery mildew incited by *Podosphaera xanthii* race S," *HortScience*, 46(6):838-840, 2011.
Ning et al., "Inheritances and location of powdery mildew resistance gene in melon Edisto47," *Euphytica*, 195:345-353, 2014.
Perchepied et al., "Relationship between loci conferring downy mildew and powdery mildew resistance in melon assessed by quantitative trait loci mapping," *Phytopathology*, 95(5):556-565, 2005.
Perin et al., "A reference map of *Cucumis melo* based on two recombinant inbred line populations," *Theor Appl Genet*, 104:1017-1034, 2002.
Pitrat, "Linkage groups in *Cucumis melo* L.," *J Hered*, 82:406-411, 1991.
Pitrat et al., "Resistance of melon to *Cucumber Vein Yellowing Virus* (CVYV)," *Cucurbitaceae*, 157-164, 2012.
Teixeira et al., "An AFLP marker linked to the Pm-1 gene that confers resistance to *Podosphaera xanthii* race 1 in *Cucumis melo*," *Genet Mol Biol*, 31(2):547-550, 2008.
Wang et al., "Powdery mildew resistance gene (Pm-AN) located in a segregation distortion region of melon LGV," *Euphytica*, 180:421-428, 2011.

(Continued)

*Primary Examiner* — Brent T Page
(74) *Attorney, Agent, or Firm* — Dentons US LLP; Matthew Madsen

(57) ABSTRACT

The present disclosure provides melon plants exhibiting resistance to powdery mildew, aphids, and cucumber vein yellowing virus (CVYV). In certain embodiments, the invention provides melon plants with powdery mildew, aphid, and CVYV resistance loci located in cis linkage on chromosome 5. In certain aspects, compositions, including novel polymorphic markers and methods for producing, breeding, identifying, and selecting plants or germplasm with a disease resistance phenotype are provided.

26 Claims, 3 Drawing Sheets
Specification includes a Sequence Listing.

(56) References Cited

OTHER PUBLICATIONS

Yuste-Lisbona et al., "Genetic linkage map of melon (*Cucumis melo* L.) and localization of a major QTL for powdery mildew resistance," *Mol Breeding*, 27:181-192, 2011.

```
                            SEQUENCE LISTING

<160> NUMBER OF SEQ ID NOS: 23

<210> SEQ ID NO 1
<211> LENGTH: 120
<212> TYPE: DNA
<213> ORGANISM: Artificial Sequence
<220> FEATURE:
<223> OTHER INFORMATION: Probe

<400> SEQUENCE: 1
ttgcaactgc aatcatggat atgtatgcaa aatgtggcaa gttggtgacr gcacggaatc      60
tgtttgacaa gatgcctcaa agaaacttgg ttgtttggaa ttcaatgatc agtgctttta    120

<210> SEQ ID NO 2
<211> LENGTH: 150
<212> TYPE: DNA
<213> ORGANISM: Artificial Sequence
<220> FEATURE:
<223> OTHER INFORMATION: Probe

<400> SEQUENCE: 2
tccatgacca aggtttacgg tattgagcct accatggagc attatggttg catgattgay      60
cttttgagtc gagcaggcca ctccgaagag gccgaggagc tcccaatgaa aatgccaacg    120
cagcctaatg caacaatctt gagttctatt                                     150

<210> SEQ ID NO 3
<211> LENGTH: 178
<212> TYPE: DNA
<213> ORGANISM: Artificial Sequence
<220> FEATURE:
<223> OTHER INFORMATION: Probe

<400> SEQUENCE: 3
catctctgtc ctcatctcca gaatctcttg ctcaacaaag tctagtcttt cttcgctctt      60
tttagccatc tccttgcgtt tgcccagatt cagtttctct kataccaatt tgatagaaca    120
ccaatatggt gactctactt tattgatatt caaacttaat tacaataaga aatgaaaa     178

<210> SEQ ID NO 4
<211> LENGTH: 121
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t

<400> SEQUENCE: 4
```

```
ngaattatnn attgctagca taannaattc cttgtatgtt tataccaatg aagaactgaa    60
ytcctatcgt agagcaccga cttgtttttc tttccagctc cgatgagtcc tcctggaaga   120
a                                                                  121
```

<210> SEQ ID NO 5
<211> LENGTH: 121
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (84)..(86)
<223> OTHER INFORMATION: n is a, c, g, or t
<400> SEQUENCE: 5

```
atttcgataa attccacttt cttggaagag atcatgactc ccgagcttga cttgttgtcg    60
ytagtctgtt gtaccagtct tgtnnnttaa cacacttgca actagtggtt agttgttacg   120
a                                                                  121
```

<210> SEQ ID NO 6
<211> LENGTH: 121
<212> TYPE: DNA
<213> ORGANISM: Artificial Sequence
<220> FEATURE:
<223> OTHER INFORMATION: Probe
<400> SEQUENCE: 6

```
tatgtttcga tgttgaatca aataatccat tatctcaatt cattttatgg ctcctatttc    60
wagattacaa acacagtaca taatgggtat ggataaatca aaactacaag tgttttaaac   120
a                                                                  121
```

<210> SEQ ID NO 7
<211> LENGTH: 121
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<400> SEQUENCE: 7

```
nnnnnnnnng ataaaaggag nnntgtggga gtgagaaata atgtaagaga agaaaatgaa    60
kgagtgaaga atagtgacat aagagaaata ggagaataag tataataatc gtaatcctaa   120
t                                                                  121
```

<210> SEQ ID NO 8
<211> LENGTH: 146
<212> TYPE: DNA
<213> ORGANISM: Artificial Sequence
<220> FEATURE:
<223> OTHER INFORMATION: Probe
<400> SEQUENCE: 8

```
agactcgatg gtttctttct aagttatctt tgcacaatgg taatttagtt tagatgtgtt    60
```

```
tytacctact tgattttatg ttgggttcag ataycttttt ygaatttgga cattttttgta    120 gcttggtttt gagtgttttg gaggtt                                          146

<210> SEQ ID NO 9
<211> LENGTH: 121
<212> TYPE: DNA
<213> ORGANISM: Artificial Sequence
<220> FEATURE:
<223> OTHER INFORMATION: Probe

<400> SEQUENCE: 9
tcagtttttt tgtttgtcga ttccataata atccctttttg cctactttttt agagactgta   60 rgaccaagga gctaggaact tttggataca caacacaggt cctctaggat gtttggctca    120
g                                                                    121

<210> SEQ ID NO 10
<211> LENGTH: 180
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 10
taacactcac atgttctgct tcaaggattt attgcggtta nccanttcga gaacatattt     60
acgaaagaat gcaatgcgtg tacaaytggt taagttatgt aatttctttt atgacatata   120
ctcaaagata ataagcatgt tttatgctag aagtgagtta tttttttatat atactcaaag  180

<210> SEQ ID NO 11
<211> LENGTH: 161
<212> TYPE: DNA
<213> ORGANISM: Artificial Sequence
<220> FEATURE:
<223> OTHER INFORMATION: Probe

<400> SEQUENCE: 11
tctgtcatat gataagactt tataactgta aaatgttaca tttatggtta ttatatcatc    60
tattataatt aactagtctc tcmtctgctt gtwgacatar ctaacacact tttagtgawa   120
cayaygaact tgygtgtcga ttttctatag tttaaacata a                        161

<210> SEQ ID NO 12
<211> LENGTH: 149
<212> TYPE: DNA
<213> ORGANISM: Artificial Sequence
<220> FEATURE:
<223> OTHER INFORMATION: Probe

<400> SEQUENCE: 12
taattaacta gtctctcmtc tgcttgtwga catarctaac acactttag tgawacayay     60 gaacttgygt gtcgattttc tatagtttaa acataagtat tgccccaagt aaaatgtggg   120
aaacagaata agtagaggct gaaagttcg                                      149

<210> SEQ ID NO 13
<211> LENGTH: 121
```

```
<212> TYPE: DNA
<213> ORGANISM: Artificial Sequence
<220> FEATURE:
<223> OTHER INFORMATION: Probe

<400> SEQUENCE: 13
aaacacagta cataatgggt atggataaat caaaactaca agtgttttaa acaagttata      60
rctttgctct ccccttcttc cttcaaataa atcaaaattt aaaatgtatt ttgttctttt     120
c                                                                    121

<210> SEQ ID NO 14
<211> LENGTH: 121
<212> TYPE: DNA
<213> ORGANISM: Artificial Sequence
<220> FEATURE:
<223> OTHER INFORMATION: Probe

<400> SEQUENCE: 14
acatcttagg aacttgcgaa ttcgggagga tactgctaaa tatcttttaa atcttgatgt      60
kaattctgct tattatgatc ccaaaactcg gtccatgcgt gaagaccctc ttcctgatgt     120
t                                                                    121

<210> SEQ ID NO 15
<211> LENGTH: 121
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t

<400> SEQUENCE: 15
nnnnnntttn aaaactataa ggtgttttcc cttagtccag gatgctcact gtgagataca      60
kaatataata acacaataga ataagaagag cagaagagta gaattaaaga tatatatatn     120
a                                                                    121

<210> SEQ ID NO 16
<211> LENGTH: 121
<212> TYPE: DNA
<213> ORGANISM: Artificial Sequence
<220> FEATURE:
<223> OTHER INFORMATION: Probe

<400> SEQUENCE: 16
aaactcgtgc ttccaaaatt ggccgagatg tacatcaaaa tcgttgataa acactctaga      60 wttgaccttta aatgccttgt caataccttg taatttgaca caagaagcaa tagaaacctt    120
c                                                                    121

<210> SEQ ID NO 17
<211> LENGTH: 121
<212> TYPE: DNA
<213> ORGANISM: Artificial Sequence
<220> FEATURE:
```

```
<223> OTHER INFORMATION: Probe
<220> FEATURE:
<221> NAME/KEY: misc_feature
<222> LOCATION: (3)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(17)
<223> OTHER INFORMATION: n is a, c, g, or t
<220> FEATURE:
<221> NAME/KEY: misc_feature
<222> LOCATION: (20)..(48)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t

<400> SEQUENCE: 17
ttnnnnnnnt ntnnnnnaan nnnnnnnnnn nnnnnnnnnn nnnnnnnnat tcaagtgtg      60 yatatcaagt gcccaagtgt gtacgtatca aatgtatatc acaggaatca agtgtgtcna    120
t                                                                    121

<210> SEQ ID NO 18
<211> LENGTH: 121
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (93)..(93)
<223> OTHER INFORMATION: n is a, c, g, or t

<400> SEQUENCE: 18
taatttgaag acaaatcaa agaaccagaa aggaatggaa aagtagaagg ataatcaaag       60
stggtgcctg agtttttgaa acgataaata ttnatccata agtgtgtgga tcccatctaa    120
a                                                                    121

<210> SEQ ID NO 19
<211> LENGTH: 121
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t

<400> SEQUENCE: 19
aagaattata aaatttatca atgctagact cttatcaacg atataatcta tcactaacag      60
rctttgagag cttatctann ttttgctata tctacaagtt cttttgcatt tgtgcngta     120 t                                                                    121

<210> SEQ ID NO 20
<211> LENGTH: 180
<212> TYPE: DNA
<213> ORGANISM: Artificial Sequence
```

```
<220> FEATURE:
<223> OTHER INFORMATION: Probe

<400> SEQUENCE: 20
gtacttgctt cgatctcttt cacgaaatcc attctcacaa tcatcgaggt ttaattcgga      60
ggaatctttt gtttttctcc catgaatcmt tcgcaagtcg attgaatcgg tagatttgat     120
tctccaatcc tcagctcaaa gattaagaag gtttggaaac tcgcgcgatc attgttcgaa     180

<210> SEQ ID NO 21
<211> LENGTH: 121
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (81)..(82)
<223> OTHER INFORMATION: n is a, c, g, or t

<400> SEQUENCE: 21
accaacaaaa gactaattga aaattttgta aaattcccca tccctagctc atgtttcgac      60
yacttgtcct cttcgtgtta nntttttttt accaatgaaa cttgcttctt atcatgaata     120
t                                                                     121

<210> SEQ ID NO 22
<211> LENGTH: 163
<212> TYPE: DNA
<213> ORGANISM: Artificial Sequence
<220> FEATURE:
<223> OTHER INFORMATION: Probe

<400> SEQUENCE: 22
gtcgcctctt agcaggacaa caacctgcaa taaaccaaaa tgtgttttga ttacatgttt      60
cttgaagaga gatgagggga tacygtgctg tagtttccta cttgcctgac tcattcgagg     120
tcggagaata ggagactgct caatgcataa agatgcagtt aaa                       163

<210> SEQ ID NO 23
<211> LENGTH: 165
<212> TYPE: DNA
<213> ORGANISM: Artificial Sequence
<220> FEATURE:
<223> OTHER INFORMATION: Probe

<400> SEQUENCE: 23
acaccttcca tgcaatgtgc agacggggat tatttctctc caagtacaaa aagaagattt      60
cttttgggta atcagaatag taatgataga aaacaaaaag atgatgccgt tttgcctggg     120
cttggtcart ctatgtctat ggttaccaat tttgatggtg agcaa                     165
```

MELON PLANTS WITH IMPROVED TRAITS

REFERENCE TO RELATED APPLICATION

This application claims the benefit of U.S. Provisional Application No. 62/381,469, filed on Aug. 30, 2016, which is incorporated herein by reference in its entirety.

FIELD OF THE INVENTION

The present invention relates to the field of agriculture and more specifically to methods and compositions for producing melon plants exhibiting improved disease resistance.

INCORPORATION OF SEQUENCE LISTING

The sequence listing that is contained in the file named "SEMB022US_ST25.txt," which is 9,386 bytes as measured in Microsoft Windows operating system and was created on Aug. 10, 2017, is filed electronically herewith and incorporated herein by reference.

BACKGROUND OF THE INVENTION

Disease resistance is an important trait in agriculture, particularly for the production of food crops. Although disease resistance alleles have been identified in melon plants, efforts to combine several disease resistance traits in a single plant line have been hindered by tightly linked or even allelic loci conferring resistance to different pathogens. This is further complicated by high densities of repeated sequences in regions of plant genomes controlling disease resistance, which can greatly reduce the possibility of developing useful genetic markers. A need therefore remains for plants comprising two or more disease resistance alleles in a cis configuration, allowing for the heterozygous deployment of one or more of the resistance alleles while maintaining resistance to the disease controlled by the remaining loci.

SUMMARY OF THE INVENTION

In one aspect, the present invention provides a melon plant of a cultivated melon plant variety comprising a chromosomal segment that comprises a first allele conferring Powdery Mildew resistance and a second allele conferring resistance to Cucumber Vein Yellowing Virus (CVYV), wherein said first allele and said second allele are configured in cis linkage on chromosome 5. In some embodiments, the chromosomal segment further comprises a third allele conferring resistance to *Aphis gossypii*. In further embodiments, the chromosomal segment is flanked by marker loci SNPmarker_23 and SNPmarker_21 on chromosome 5, or flanked by marker loci SNPmarker_1 and SNPmarker_16 on chromosome 5, or flanked by marker loci SNPmarker_9 and SNPmarker_22 on chromosome 5. In certain embodiments, plants of the invention comprise an introgressed chromosomal segment from a Powdery Mildew resistant parent plant at a locus genetically linked to marker locus SNPmarker_1 on chromosome 5. Plants of the invention may comprise an introgressed chromosomal segment from Hale's Best Jumbo-AR at a locus genetically linked to marker locus SNPmarker_1 on chromosome 5. In further embodiments, plants of the invention comprise an introgressed chromosomal segment from a CVYV resistant parent plant at a locus genetically linked to marker locus SNPmarker_16 on chromosome 5. In further embodiments, plants of the invention comprise an introgressed chromosomal segment from a CVYV resistant parent plant at a locus genetically linked to marker locus SNPmarker_22 on chromosome 5 Plants of the invention may comprise an introgressed chromosomal segment from PI164323 at a locus genetically linked to marker locus SNPmarker_16 on chromosome 5. In yet further embodiments, plants of the invention comprise an introgressed chromosomal segment from a Powdery Mildew resistant parent plant at marker locus SNPmarker_1 on chromosome 5 and an introgressed chromosomal segment from a CVYV resistant parent plant at marker locus SNPmarker_16 on chromosome 5, or plants of the invention comprise an introgressed chromosomal segment from Hale's Best Jumbo-AR at a locus genetically linked to marker locus SNPmarker_1 on chromosome 5 and an introgressed chromosomal segment from PI164323 at a locus genetically linked to marker locus SNPmarker_16 and/or SNPmarker_22 on chromosome 5.

In other embodiments, plants of the invention comprise a chromosomal segment wherein a representative sample of seed comprising said chromosomal segment has been deposited under Accession No. PTA-123300 and under Accession. No. PTA-124003. The invention further provides plant parts of the melon plants provided herein, for example wherein the plant part is a cell, a seed, a root, a stem, a leaf, a fruit, a flower, or pollen.

In another aspect, the present invention provides a method for producing a melon plant exhibiting resistance to Powdery Mildew and CVYV, comprising: a) crossing a melon plant provided herein with itself or with a second melon plant of a different genotype to produce one or more progeny plants; and b) selecting a progeny plant comprising said chromosomal segment.

In some embodiments, selecting said progeny plant comprises marker-assisted selection. In further embodiments, marker-assisted selection comprises detecting at least one allele at a genomic locus flanked by marker loci SNPmarker_23 and SNPmarker_21, or detecting at least one allele at a genomic locus flanked by marker loci SNPmarker_1 and SNPmarker_16, or detecting at least one allele at a genomic locus flanked by marker loci SNPmarker_9 and SNPmarker_22. In yet further embodiments, marker-assisted selection comprises detecting at least one allele at a locus genetically linked to a marker locus selected from the group consisting of: SNPmarker_1 (SEQ ID NO: 1), SNPmarker_2 (SEQ ID NO: 2), SNPmarker_3 (SEQ ID NO: 3), SNPmarker_4 (SEQ ID NO: 4), SNPmarker_5 (SEQ ID NO: 5), SNPmarker_6 (SEQ ID NO: 6), SNPmarker_7 (SEQ ID NO: 7), SNPmarker_8 (SEQ ID NO: 8), SNPmarker_9 (SEQ ID NO: 9), SNPmarker_1 (SEQ ID NO: 10), SNPmarker_11 (SEQ ID NO: 11), SNPmarker_12 (SEQ ID NO: 12), SNPmarker_13 (SEQ ID NO: 13), SNPmarker_14 (SEQ ID NO: 14), SNPmarker_15 (SEQ ID NO: 15), SNPmarker_16 (SEQ ID NO: 16), SNPmarker_17 (SEQ ID NO: 17), SNPmarker_18 (SEQ ID NO: 18), SNPmarker_19 (SEQ ID NO: 19), SNPmarker_20 (SEQ ID NO: 20), SNPmarker_21 (SEQ ID NO: 21), SNPmarker_22 (SEQ ID NO: 22), and SNPmarker_23 (SEQ ID NO:23). For example, marker-assisted selection may comprise detecting at least one allele at a locus genetically linked to a marker locus selected from the group consisting of: SNPmarker_1 and SNPmarker_20. A progeny plant provided by the invention may be an F2-F6 progeny plant. Producing a progeny plant may comprise backcrossing, for example wherein backcrossing comprises from 2-7 generations of backcrossing.

In a further aspect, the invention provides a method of selecting a melon plant exhibiting resistance to Powdery Mildew and CVYV, comprising: a) crossing a melon plant provided herein with itself or with a second melon plant of a different genotype to produce one or more progeny plants; and b) selecting a progeny plant comprising said chromosomal segment. In some embodiments, selecting said progeny plant comprises marker-assisted selection. In further embodiments, marker-assisted selection comprises detecting at least one allele at a genomic locus flanked by marker loci SNPmarker_23 and SNPmarker_21, or detecting at least one allele at a genomic locus flanked by marker loci SNPmarker_1 and SNPmarker_16, or detecting at least one allele at a genomic locus flanked by marker loci SNPmarker_9 and SNPmarker_22. In yet further embodiments, marker-assisted selection comprises detecting at least one allele at a locus genetically linked to a marker locus selected from the group consisting of: SNPmarker_1 (SEQ ID NO: 1), SNPmarker_2 (SEQ ID NO: 2), SNPmarker_3 (SEQ ID NO: 3), SNPmarker_4 (SEQ ID NO: 4), SNPmarker_5 (SEQ ID NO: 5), SNPmarker_6 (SEQ ID NO: 6), SNPmarker_7 (SEQ ID NO: 7), SNPmarker_8 (SEQ ID NO: 8), SNPmarker_9 (SEQ ID NO: 9), SNPmarker_10 (SEQ ID NO: 10), SNPmarker_11 (SEQ ID NO: 11), SNPmarker_12 (SEQ ID NO: 12), SNPmarker_13 (SEQ ID NO: 13), SNPmarker_14 (SEQ ID NO: 14), SNPmarker_15 (SEQ ID NO: 15), SNPmarker_16 (SEQ ID NO: 16), SNPmarker_17 (SEQ ID NO: 17), SNPmarker_18 (SEQ ID NO: 18), SNPmarker_19 (SEQ ID NO: 19), SNPmarker_20 (SEQ ID NO: 20), SNPmarker_21 (SEQ ID NO: 21), SNPmarker_22 (SEQ ID NO: 22), and SNPmarker_23 (SEQ ID NO:23). For example, marker-assisted selection may comprise detecting at least one allele at a locus genetically linked to a marker locus selected from the group consisting of: SNPmarker_1 and SNPmarker_20. A progeny plant provided by the invention may be an F2-F6 progeny plant. Producing a progeny plant may comprise backcrossing, for example wherein backcrossing comprises from 2-7 generations of backcrossing.

In yet a further aspect, the invention provides plants produced by the methods provided herein, or a plant part of said plant selected from the group consisting of a cell, a seed, a root, a stem, a leaf, a fruit, a flower, and pollen.

DETAILED DESCRIPTION

Figure 1:
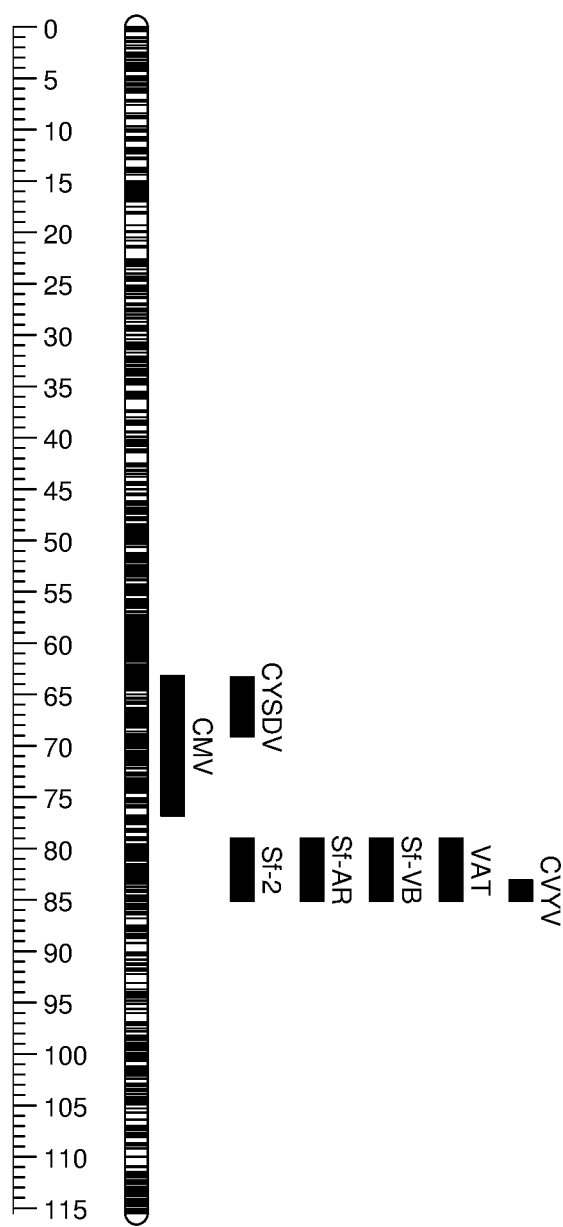
FIG. 1: Shows a genomic region on chromosome 5 comprising tightly linked disease resistance loci. This area of the chromosome comprises resistance loci for cucurbit yellow stunting disorder virus (CYSDV), cucumber mosaic virus (CMV), cucumber vein yellowing virus (CVYV), aphid resistance (VAT), and powdery mildew (PM) resistance (Sf-2, Sf-AR, and Sf-VB), situated within a 20 cM span.

Although alleles conferring resistance to Powdery Mildew (PM), Cucumber Vein Yellowing Virus (CVYV), and melon aphid (*Aphis gossypii*) have been identified in melon plants, efforts to combine these disease resistance traits in a single plant line have been unsuccessful due to the tight linkage of these loci. In addition, the high density of repeated sequence in this region makes the development of genetic markers that could successfully assist in marker assisted breeding extremely difficult. In particular, PM and CVYV loci on chromosome 5 of the melon genome were believed prior to the instant disclosure to be so tightly linked as to be allelic, such that deployment of a favorable allele at a first locus could preclude deployment of a favorable allele conferring resistance to a second pathogen. The tight linkage between these disease resistance loci is further problematic because broad spectrum PM resistance requires heterozygous deployment of multiple alleles directed to different PM races on each chromosome. This requirement for heterozygous deployment has thus far prevented deployment of PM resistance alleles together with CVYV resistance alleles, leaving melon hybrids unacceptably susceptible to either CVYV or several powdery mildew races. This is of particular concern in the areas of the world, such as the Mediterranean region, where these diseases co-occur.

Contrary to the previous belief in the art that CVYV and PM resistance loci were so tightly linked as to be allelic, the present inventors have successfully produced melon plants comprising CVYV and PM resistance alleles in a cis configuration. For the first time, the inventors have demonstrated that the powdery mildew and CYVY resistance loci are not allelic, allowing for the stacking of these traits while deploying PM resistance alleles on both chromosomes. The invention also provides for the first time melon plants comprising CVYV, PM, and aphid resistance alleles in a cis configuration on chromosome 5. Methods of producing melon plants exhibiting resistance to CVYV, PM, and melon aphids, as well as novel markers for tracking disease resistance alleles during plant breeding are further provided. The invention therefore represents a significant advance in the art by combining these disease resistance traits in plant lines capable of acting as donor parents for introgression of disease resistance into any desired melon genotype.

The invention additionally provides melon plants comprising PM, CVYV, and aphid resistance alleles in a cis configuration on chromosome 5, and further comprising additional PM resistance alleles in trans, such that the plants exhibit broad spectrum resistance to PM, while also exhibiting resistance to CVYV and aphids. In further embodiments, the invention provides melon plants comprising a genetic region between SNPmarker_21 and SNPmarker_23 conferring PM, CVYV, and aphid resistance, where the resistance alleles are in a cis configuration. In further embodiments, the invention provides melon plants comprising a genetic region between SNPmarker_21 and SNPmarker_23 conferring PM, CVYV, and aphid resistance, where the resistance alleles are in a cis configuration, and wherein the plant further comprises a similar genetic region between SNPmarker_21 and SNPmarker_23 in trans configuration, where the PM allele, which is in cis configuration with a CVYV resistance allele and optionally an aphid resistance allele, is different from the PM allele of the first PM, CVYV, aphid resistance combination, such that the plants exhibit broad spectrum resistance to PM, while also exhibiting resistance to CVYV and aphids. In further embodiments, the invention provides melon plants comprising PM resistance donor DNA at marker SNPmarker_1 at 81.50 cM, and CVYV resistance donor DNA at marker SNPmarker_16 at 83.1 cM. In some embodiments, plants of the present invention comprise PM resistance donor DNA from Hale's Best Jumbo-AR (McCreight et al. 1984) at marker SNPmarker_1, and CVYV resistance donor DNA from PI164323, which is available through the U.S. National Plant Germplasm System of the USDA, at marker SNPmarker_16. The invention further provides plants comprising PM and CVYV resistance alleles as a result of a recombination event occurring between markers SNPmarker_1 and SNPmarker_21. In certain embodiments, melon plants of the invention comprise PM and CVYV resistance alleles as a result of a recombination event occurring between markers SNPmarker_1 and SNPmarker_16. In certain embodiments, melon plants of the invention comprise PM and CVYV resistance alleles as a result of a recombination event occurring between markers SNPmarker_1 and SNPmarker_18. In certain embodiments, melon plants of the invention comprise PM and CVYV resistance alleles as a result of a recombination event occurring between markers SNPmarker_9 and SNPmarker_22

The invention further provides novel trait-linked markers that can be used to produce, detect, or track plants comprising PM, CVYV, and aphid resistance alleles during plant breeding. In particular embodiments, the invention provides the markers shown in Table 2 and FIG. 3, including markers within a genomic region flanked by markers SNPmarker_1 and SNPmarker_16. Other embodiments of the invention provide novel markers SNPmarker_1, SNPmarker_19, SNPmarker_9, SNPmarker_21, SNPmarker_20, SNPmarker_22, and SNPmarker_23 which are useful in detection and tracking of plants comprising PM, CVYV, and aphid resistance during plant breeding. Marker status for PM resistance donor (Hale's Best Jumbo AR) and CVYV resistance donor (PI64323), as well as several hybrid plants, is shown in Table 2.

In other embodiments, the invention provides methods of producing melon plants comprising CVYV, PM, and aphid resistance alleles in a cis configuration on chromosome 5 by selecting or breeding plants having favorable alleles at markers within or genetically linked to the chromosomal segments disclosed herein. In some embodiments, the invention provides methods of selecting or breeding plants comprising detecting at least one allele at a locus within a genomic segment flanked by markers SNPmarker_23 and SNPmarker_21. In certain embodiments, the methods of the invention comprise detecting a marker within a genomic region flanked by marker loci SNPmarker_19 and SNPmarker_21, for example by detecting one or more of markers SNPmarker_1, SNPmarker_19, SNPmarker_9, SNPmarker_16, SNPmarker_21, SNPmarker_20, and SNPmarker_22.

I. Genomic Regions, Alleles, and Polymorphisms Associated with Disease Resistance in Melon Disease loci are located at various places of the genome, but some genomic regions have a higher concentration of disease loci than others. For melon, such a region exists on chromosome 5. This area of the chromosome contains resistance loci for CYSDV, CVYV, CMV, powdery mildew, and aphid resistance situated within a 20 cM span (FIG. 1). Resistance loci for PM and CVYV on chromosome 5 are tightly genetically linked, and it was therefore believed in the art prior to the instant disclosure that the CVYV locus was allelic to the Sf-AR locus (and other powdery mildew resistance alleles at this genomic position). Further complicating efforts to obtain plants comprising favorable alleles for PM, CVYV, and melon aphid resistance, or to map this region, is the fact the disease resistance region on chromosome 5 exhibits a high density of repeats.

The tight linkage of CVYV and PM is further problematic because known PM resistance alleles each only confer resistance to a subset of PM races, and must be deployed on both chromosomes to provide an acceptably broad spectrum of PM resistance. If CVYV and PM were allelic, as was previously believed in the art, it would not be possible to deploy PM resistance alleles on both chromosomes in addition to a CVYV resistance allele. This would leave melon hybrids unacceptably susceptible to either CVYV or several powdery mildew races.

Powdery Mildew

Powdery Mildew (*Podoshaera xanthii*) causes a destructive fungal infection in melon. PM resistance loci have been identified on chromosomes 2, 5, 9 and 12, each conferring resistance to a specific set of powdery mildew races or pathotypes. Each resistance locus can also have multiple alleles, each allele conferring resistance to a specific spectrum of PM races. For example, the PM resistance locus on chromosome 5 (which co-localizes with the aphid resistance locus vat; FIG. 1) has several alleles. The first known allele at this position was Sf-2 (Pm-W or PmW), which came from breeding line WMR-29 (Pitrat, 1991; Perin, 2002). Melon breeding lines coupling powdery mildew resistance to aphid resistance have been developed using the Sf-2 allele, for example Hale's Best Jumbo-AR (Allele Sf-AR). Two further alleles at this position on chromosome 5, Sf-VB and Sf-SV, were later discovered by the inventors. Additional sources of PM resistance alleles on chromosome 5 include PI124112 (Allele: Pm-V.1; Perchepied, 2005), ANO2 (Allele: Pm-AN; Wang, 2011), Edisto47 (Allele: Pm-Edisto47-2; Ning, 2014), and TGR-1551 (Allele: Pm-R; Yuste-Lisbona, 2011). In other embodiments of the invention, the method of the invention is used to track recombination between a CVYV resistance allele and one of the previously described PM loci.

Like the loci on different chromosomes, each of these alleles is defined by their own resistance profile to powdery mildew (Table 1). The Sf-AR resistance allele, like the Sf-2 allele does not provide resistance to all powdery mildew races (Table 1). In order to produce a melon that is fully resistant to powdery mildew, it is therefore necessary to combine different resistance loci and alleles in a single melon line. This is a time consuming and costly process that provides no expectation of success, as the stacking of multiple loci both requires selection of the new locus, while also maintaining previously introgressed loci. This difficult process is further hindered by the need to maintain multiple additional commercial and agronomic traits during selection of a melon line exhibiting a favorable PM resistance trait. As a further obstacle, breeding and selection of plants exhibiting favorable phenotypes for several traits is greatly complicated when loci conferring various traits are tightly genetically linked, such as on chromosome 5.

TABLE 1

Resistance to PM Races conferred by several PM resistance alleles.

| | Powdery mildew races | | | | | |
|---|---|---|---|---|---|---|
| | 0 | 1 | 2 | 3 | 5 | 3-5 |
| "Iran-H" | + + | + | + | + | + | + |
| — | R (+) | + | + | + | + | + |
| Pm-1 (ch.2) | R | R | + | + | + | + |
| Pm-2 (ch.12) | R | R | R | + | R | + |
| Sf-2 (PmW) | R | R | R | R | + | + |
| | A  B | A  B | A  B | A  B | A  B | A  B |
| Sf-AR | R (+) | R  + | R  + | R  + | R  + | R  + |
| | − + − + | − + − + | − + − + | − + − + | − + − + | − + − + |
| Sf-VB | R | R + R + | R + R + | R + R + | R + R + | R + R + |

Cucumber Vein Yellowing Virus

Figure 2:
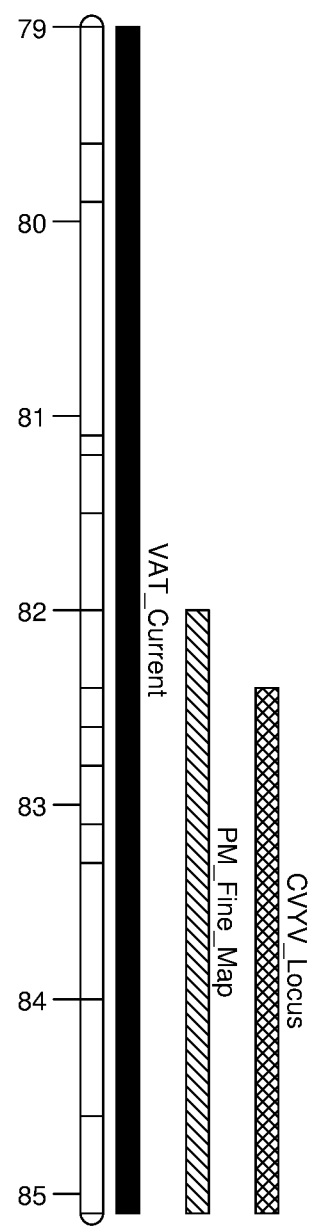
FIG. 2: Shows fine mapping of VAT, PM, and CVYV resistance loci on chromosome 5.

CVYV is an ipomovirus from the family of Potyviridae that is transmitted by the whitefly *Bemisia tabaci*. This disease currently causes significant losses to melon production in the Mediterranean region. Only two resistant *Cucumis melo* sources have been described with dominant alleles: CUC6491 and PI164323 (WO20100257447(A1), Pitrat et al., 2012). The resistance to CVYV from CUC6491 has been mapped to linkage group 9, while the resistance of PI165323 has been mapped by the present inventors to chromosome 5 in the same region as where Sf-AR is located (FIG. 2). Because these disease resistance loci are co-localized, it was believed prior to the instant disclosure that the CVYV locus was allelic to the Sf-AR locus and other powdery mildew resistance alleles. This was problematic due to the need to deploy PM resistance on both chromosomes in order to confer resistance to the full complement of fungal races. Deploying PM resistance on both chromosomes was believed to prevent deploying the CVYV resistance allele from PI164323 in the hybrid, which was thought to be allelic with PM resistance alleles. This would leave melon hybrids unacceptably susceptible to either CVYV or several powdery mildew races.

Surprisingly, and in direct contrast to the previous belief that PM and CVYV resistance loci are allelic, the present inventors have shown for the first time that PM and CVYV disease resistance loci on chromosome 5 can be configured in cis. The invention therefore provides novel chromosomal segments comprising PM and CVYV resistance alleles, and melon plants comprising these chromosomal segments. The coupling of these two resistance alleles allows breeders to transfer a single resistance stack between plants, which greatly improves the efficiency and efficacy of breeding for resistant plants compared to when breeders must combine resistance loci from different sources and/or at different chromosomes. The plants provided by the invention exhibit a broad spectrum of PM resistance coupled with resistance to CVYV. Novel polymorphic markers associated with these novel chromosomal segments are further provided.

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of the newly provided chromosomal segments comprising PM, CVYV, and aphid resistance loci disclosed herein into cultivated lines. In certain embodiments, the invention provides the markers set forth in Table 2 and FIG. 3. Further embodiments of the invention provide novel markers, SNPmarker_1, SNPmarker_2, SNPmarker_3, SNPmarker_4, SNPmarker_5, SNPmarker_6, SNPmarker_7, SNPmarker_8, SNPmarker_9, SNPmarker_10, SNPmarker_11, SNPmarker_12, SNPmarker_13, SNPmarker_14, SNPmarker_15, SNPmarker_16, SNPmarker_17, SNPmarker_18, SNPmarker_19, SNPmarker_20, SNPmarker_21, and SNPmarker_22 which are useful in detection and tracking of plants comprising PM and CVYV, and aphid resistance in cis linkage during plant breeding.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistant phenotype.

Melon plants comprising one or more introgressed regions associated with a desired phenotype wherein at least 10%, 25%, 50%, 75%, 90%, or 99% of the remaining genomic sequences carry markers whose alleles match the recurrent parent genotype outside of the region targeted for disease resistance introgression are also provided. Melon plants comprising an introgressed region closely linked to, or adjacent to, the genomic regions and markers provided herein and associated with a disease resistance phenotype are also provided.

The plants of the invention can be made in absence of marker assisted selection by crossing plants lacking resistance to PM, CVYV and aphids to plants of line MZZ C215-0015MO or MZZ-C216-0017MO, which have been deposited at the American Type Culture Collection (ATCC), 10801 University Blvd., Manassas, Va. 20110-2209, under ATCC Accession No. PTA-123300 and Accession No. PTA-124003, respectively. The offspring of this cross is then tested for PM, CVYV and aphid resistance. Those plants displaying the combined resistance against PM, CVYV and aphids are selected as these contain the disease resistances in cis linkage of the invention on chromosome 5.

III. Development of Disease Resistant Melon Varieties

For most breeding objectives, commercial breeders work within germplasm that is "cultivated," "cultivated type" or "elite." As used herein, "elite" or "cultivated" variety means a variety that has resulted from breeding and selection for superior agronomic performance for use in agriculture. This germplasm is easier to breed because it generally performs well when evaluated for horticultural performance. A number of cultivated melon types have been developed which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. In melon plants, non-cultivated plant types can provide alleles associated with disease resistance. However, these non-cultivated types may have poor horticultural qualities such as vulnerability to certain deleterious traits or diseases.

The process of introgressing desirable resistance genes from non-cultivated lines into elite cultivated lines, while avoiding problems with linkage drag or low heritability, is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. The process of introgressing genomic regions from non-cultivated lines can be greatly facilitated by the availability of accurate markers for marker-assisted selection (MAS).

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, Applicants' discovery of accurate markers associated with disease resistance facilitates the development of melon plants having beneficial phenotypes. For example, seed can be genotyped using the markers of the present invention in order to select for plants comprising desired genomic regions associated with disease resistance, without the need for growing plants to maturity to evaluate phenotype. Moreover, MAS allows identification of plants homozygous or heterozygous for a desired introgression.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among melon species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics*, 8(2), 271-278), denaturing gradient gel electrophoresis (Myers (1985) EPO 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al., *Biotechniques* 12(1), 82-87, 1992), or PCR amplification of multiple specific alleles (PAMSA; Dutton and Sommer, *Biotechniques*, 11(6), 700-7002, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a melon plant a genotype associated with disease resistance, identify a melon plant with a genotype associated with disease resistance, and to select a melon plant with a genotype associated with disease resistance. In certain embodiments of methods of the invention, polymorphic nucleic acids can be used to produce a melon plant that comprises in its genome an introgressed locus associated with disease resistance. In certain embodiments of the invention, polymorphic nucleic acids can be used to breed progeny melon plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in melon plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003); Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996, 476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

A deposit of melon line MZZ C215-0015MO, which is disclosed herein and referenced in the claims, was made with the American Type Culture Collection (ATCC), 10801 University Blvd., Manassas, Va. 20110-2209. The date of deposit was Jul. 12, 2016, and the accession number for the deposited seeds is ATCC Accession No. PTA-123300. All restrictions upon the deposit have been removed, and the deposit is intended to meet all of the requirements of 37 C.F.R. § 1.801-1.809. The deposit will be maintained in the depository for a period of 30 years, or 5 years after the last request, or for the effective life of the patent, whichever is longer, and will be replaced if necessary during that period.

A deposit of melon line MZZ-C216-0017MO, which is disclosed herein and referenced in the claims, was made with the American Type Culture Collection (ATCC), 10801

University Blvd., Manassas, Va. 20110-2209. The date of deposit was Feb. 21, 2017, and the accession number for the deposited seeds is ATCC Accession No. PTA-124003. All restrictions upon the deposit have been removed, and the deposit is intended to meet all of the requirements of 37 C.F.R. § 1.801-1.809. The deposit will be maintained in the depository for a period of 30 years, or 5 years after the last request, or for the effective life of the patent, whichever is longer, and will be replaced if necessary during that period.

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which melon plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of melon breeding. An "elite population" is an assortment of elite individuals or varieties that can be used to represent the state of the art in terms of agronomically superior genotypes of a given crop species, such as melon. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked" or "genetically linked," when used in the context of nucleic acid markers and/or genomic regions, means that the markers and/or genomic regions are located in proximity on the same linkage group or chromosome such that they tend to segregate together at meiosis.

As used herein, "resistance locus" means a locus associated with resistance or tolerance to disease. For instance, a resistance locus according to the present invention may, in certain embodiments, control resistance or susceptibility to PM, CVYV, or aphids.

As used herein, "resistance allele" means the nucleic acid sequence associated with resistance or tolerance to disease.

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

EXAMPLES

Example 1

Identification of CVYV Resistance Locus

A mapping population was generated from a cross between SPA-1007-AN (susceptible)×PI164323 (resistant) to determine the location of the CVYV resistance locus. An F4 population from this cross was genotypically and phenotypically analyzed, which led to the identification of a major quantitative trait locus (QTL) on chromosome 5 in the 77.8 to 86.9 cM region on a proprietary genetic map, which is aligned with the public map (e.g. Diaz, et al., 2015) at the chromosome level. Marker sequences allow those skilled in the art to identify the marker locations on any public genome, such as the genome assembly by Garcia-Mas et al 2012, which has been improved by Argyris, et al., 2015. The genomic region within the QTL lacked existing polymorphic markers, an additional set of SNPs in this region was identified to allow fine-mapping of the CVYV location (Table 2). The population was re-genotyped with this new marker set. Marker-trait associations were estimated for 153 lines using the existing phenotypic data. The analysis was conducted using Scanone in Rqtl (Broman, et al. *Bioinformatics* 9:889-890, 2003). 1000 permutations were calculated to define the LOD thresholds and from those data the markers most highly associated with the CVYV trait were identified using two different modeling approaches: (1) a non-parametric model, which was an extension of the Kruskal-Wallis-test; and (2) a normal model, which assumes that the residual phenotypic variation follows a normal distribution, using both the maximum-likelihood method from the expectation-maximization algorithm and the single-marker regression method. This allowed the identification of trait associated markers.

TABLE 2

Markers developed within the CVYV resistance region.

| Location | Marker Designation | SEQ ID NO. | Full Sequence |
|---|---|---|---|
| 81.501659 | SNPmarker_1 | 1 | TTGCAACTGCAATCATGGATATGTATGCAAAATG TGGCAAGTTGGTGAC[A/G]GCACGGAATCTGTT TGACAAGATGCCTCAAAGAAACTTGGTTGTTTGG AATTCAATGATCAGTGCTTTTA |
| 81.615042 | SNPmarker_2 | 2 | TCCATGACCAAGGTTTACGGTATTGAGCCTACCA TGGAGCATTATGGTTGCATGATTGA[C/T]CTTT TGAGTCGAGCAGGCCACTCCGAAGAGGCCGAGGA GCTCCCAATGAAAATGCCAACGCAGCCTAATGCA ACAATCTTGAGTTCTATT |
| 81.615042 | SNPmarker_3 | 3 | CATCTCTGTCCTCATCTCCAGAATCTCTTGCTCA ACAAAGTCTAGTCTTTCTTCGCTCTTTTTAGCCA TCTCCTTGCGTTTGCCCAGATTCAGTTTCTCT [G/T]ATACCAATTTGATAGAACACCAATATGGT GACTCTACTTTATTGATATTCAAACTTAATTACA ATAAGAAATGAAAA |
| 81.69 | SNPmarker_4 | 4 | NGAATTATNNATTGCTAGCATAANNAATTCCTTG TATGTTTATACCAATGAAGAACTGAA[C/T]TCC TATCGTAGAGCACCGACTTTGTTTTCTTTCCAGC TCCGATGAGTCCTCCTGGAAGAA |
| 81.81 | SNPmarker_5 | 5 | ATTTCGATAAATTCCACTTTCTTGGAAGAGATCA TGACTCCCGAGCTTGACTTGTTGTCG[C/T]TAG TCTGTTGTACCAGTCTTGTNNNTTAACACACTTG CAACTAGTGGTTAGTTGTTACGA |
| 81.961915 | SNPmarker_6 | 6 | TATGTTTCGATGTTGAATCAAATAATCCATTATC TCAATTCATTTTATGGCTCCTATTTC[A/T]AGA TTACAAACACAGTACATAATGGGTATGGATAAAT CAAAACTACAAGTGTTTTAAACA |
| 82.2 | SNPmarker_7 | 7 | NNNNNNNNNNGATAAAAGGAGNNNTGTGGGAGTGA GAAATAATGTAAGAGAAGAAAATGAA[G/T]GAG TGAAGAATAGTGACATAAGAGAAATAGGAGAATA AGTATAATAATCGTAATCCTAAT |
| 82.354217 | SNPmarker_8 | 8 | AGACTCGATGGTTTCTTTCTAAGTTATCTTTGCA CAATGGTAATTTAGTTTAGATGTGTTT[C/T]TA CCTACTTGATTTTATGTTGGGTTCAGATAYCTTT TTYGAATTTGGACATTTTTGTAGCTTGGTTTTGA GTGTTTTGGAGGTT |
| 82.354217 | SNPmarker_9 | 9 | TCAGTTTTTTTGTTTGTCGATTCCATAATAATCC CTTTTGCCTACTTTTTAGAGACTGTA[G/A]GAC CAAGGAGCTAGGAACTTTTGGATACACAACACAG GTCCTCTAGGATGTTTGGCTCAG |
| 82.388274 | SNPmarker_10 | 10 | TAACACTCACATGTTCTGCTTCAAGGATTTATTG CGGTTANCCANTTCGAGAACATATTTACGAAAGA ATGCAATGCGTGTACAA[C/T]TGGTTAAGTTAT GTAATTTCTTTTATGACATATACTCAAAGATAAT AAGCATGTTTTATGCTAGAAGTGAGTTATTTTTT ATATATACTCAAAG |
| 82.6 | SNPmarker_11 | 11 | TCTGTCATATGATAAGACTTTATAACTGTAAAAT GTTACATTTATGGTTATTATATCATCTATTATAA TTAACTAGTCTCTC[A/C]TCTGCTTGTWGACAT ARCTAACACACTTTTAGTGAWACAYAYGAACTTG YGTGTCGATTTTCTATAGTTTAAACATAA |
| 82.6 | SNPmarker_12 | 12 | TAATTAACTAGTCTCTCMTCTGCTTGTWGACATA RCTAACACACTTTTAGTGAWACAYAYGAACTTG [C/T]GTGTCGATTTTCTATAGTTTAAACATAAG TATTGCCCCAAGTAAAATGTGGGAAACAGAATAA GTAGAGGCTGAAAGTTCG |
| 82.61 | SNPmarker_13 | 13 | AAACACAGTACATAATGGGTATGGATAAATCAAA ACTACAAGTGTTTTAAACAAGTTATA[A/G]CTT TGCTCTCCCCTTCTTCCTTCAAATAAATCAAAAT TTAAAATGTATTTTGTTCTTTTC |

TABLE 2-continued

Markers developed within the CVYV resistance region.

| Location | Marker Designation | SEQ ID NO. | Full Sequence |
|---|---|---|---|
| 82.77 | SNPmarker_14 | 14 | ACATCTTAGGAACTTGCGAATTCGGGAGGATACT GCTAAATATCTTTTAAATCTTGATGT[G/T]AAT TCTGCTTATTATGATCCCAAAACTCGGTCCATGC GTGAAGACCCTCTTCCTGATGTT |
| 83.04 | SNPmarker_15 | 15 | NNNNNNNTTTNAAAACTATAAGGTGTTTTCCCTTA GTCCAGGATGCTCACTGTGAGATACA[G/T]AAT ATAATAACACAATAGAATAAGAAGAGCAGAAGAG TAGAATTAAAGATATATATATNA |
| 83.138821 | SNPmarker_16 | 16 | AAACTCGTGCTTCCAAAATTGGCCGAGATGTACA TCAAAATCGTTGATAAACACTCTAGA[A/T]TTG ACCTTAAATGCCTTGTCAATACCTTGTAATTTGA CACAAGAAGCAATAGAAACCTTC |
| 83.138821 | SNPmarker_17 | 17 | TTNNNNNNNNTNTNNNNNAANNNNNNNNNNNNNNN NNNNNNNNNNNNNNNATTTCAAGTGTG[C/T]ATA TCAAGTGCCCAAGTGTGTACGTATCAAATGTATA TCACAGGAATCAAGTGTGTCNAT |
| 83.138821 | SNPmarker_18 | 18 | TAATTTGAAGGACAAATCAAAGAACCAGAAAGGA ATGGAAAAGTAGAAGGATAATCAAAG[C/G]TGG TGCCTGAGTTTTTGAAACGATAAATATTNATCCA TAAGTGTGTGGATCCCATCTAAA |
| 81.14 | SNPmarker_19 | 19 | AAGAATTATAAAATTTATCAATGCTAGACTCTTA TCAACGATATAATCTATCACTAACAG[A/G]CTT TGAGAGCTTATCTANNTTTTGCTATATCTACAAG TTCTTTTGCATTTTGTGCNGTAT |
| 85.094807 | SNPmarker_20 | 20 | GTACTTGCTTCGATCTCTTTCACGAAATCCATTC TCACAATCATCGAGGTTTAATTCGGAGGAATCTT TTGTTTTTTCTCCCATGAATC[A/C]TTCGCAAG TCGATTGAATCGGTAGATTTGATTCTCCAATCCT CAGCTCAAAGATTAAGAAGGTTTGGAAACTCGCG CGATCATTGTTCGAA |
| 85.123786 | SNPmarker_21 | 21 | ACCAACAAAAGACTAATTGAAAATTTTGTAAAAT TCCCCATCCCTAGCTCATGTTTCGAC[C/T]ACT TGTCCTCTTCGTGTTANNTTTTTTTTACCAATGA AACTTGCTTCTTATCATGAATAT |
| 84.04 | SNPmarker_22 | 22 | GTCGCCTCTTAGCAGGACAACAACCTGCAATAAA CCAAAATGTGTTTTGATTACATGTTTCTTGAAGA GAGATGAGGCTGATAC[C/T]GTGCTGTAGTTTC CTACTTGCCTGACTCATTCGAGGTCGGAGAATAG GAGACTGCTCAATGCATAAAGATGCAGTTAAA |
| 79.0 | SNPmarker_23 | 23 | ACACCTTCCATGCAATGTGCAGACGGGGATTATT TCTCTCCAAGTACAAAAAGAAGATTTCTTTTGGG TAATCAGAATAGTAATGATAGAAAACAAAAAGAT GATGCCGTTTTGCCTGGGCTTGGTCA[A/G]TCT ATGTCTATGGTTACCAATTTTGATGGTGAGCAA |

Example 2

Coupling of CVYV and Sf-AR Loci

To better understand the linkage and/or allelism of CVYV and Sf-AR, BC1F2 families were generated from a cross between Hale's-Best-Jumbo-AR (resistant to powdery mildew and melon aphid comprising the Sf-AR locus) and PI164323 (CVYV-resistant). 7080 BC1F2 seeds were chipped and genotyped. From those 7080 seeds, 294 seeds had a recombination event in the genetic interval of 81.5-85.1 cM, the region to which both Sf-AR and CVYV were mapped. Of these, 215 families were selected for phenotyping. In the crosses, PI164323 was used as the recurrent parent fixing the CVYV locus, thus BC1F2 families carrying a recombination event that coupled Sf-AR and CVYV resistance would show complete resistance to CVYV and intermediate or better resistance to powdery mildew in the same plant in the phenotyping test.

Figure 3:
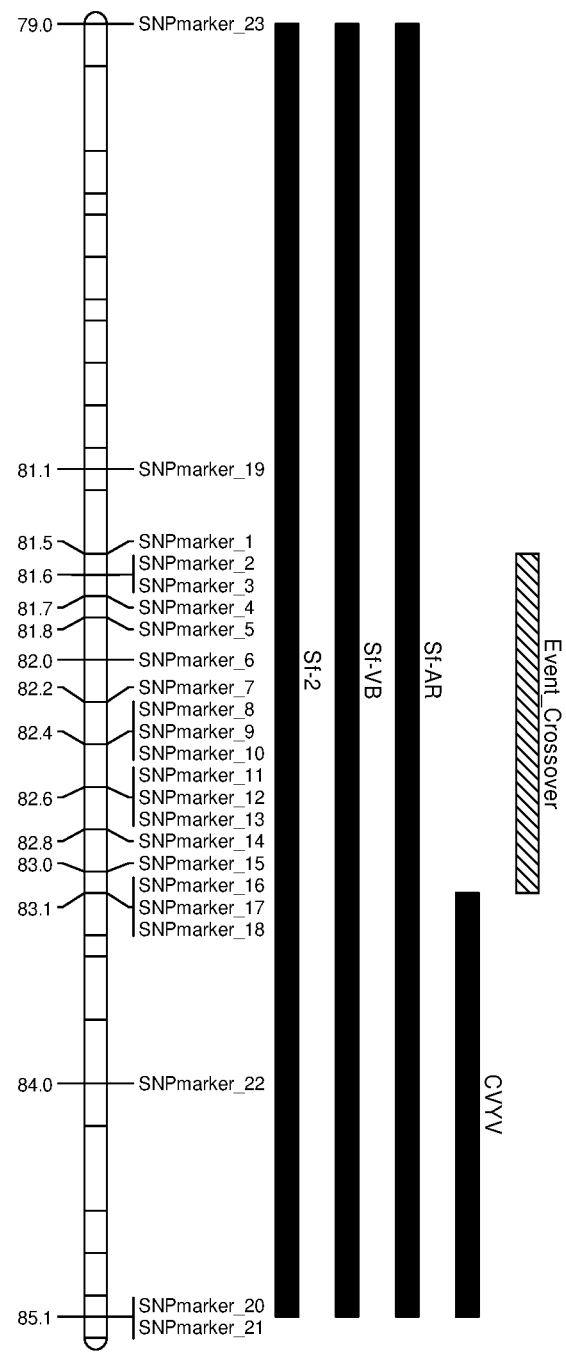
FIG. 3: Shows newly identified polymorphic markers used to map the Sf-AR, Sf-VB, Sf-2, and CVYV disease resistance loci on chromosome 5.

Disease bioassays were conducted at several locations. For the CVYV bioassay, a randomized complete block design with 3 replicates and 9 plants per replicate was used. Of the 215 families assayed, only 174 families showed full resistance to CVYV. Those 174 families were subsequently tested for powdery mildew resistance in a leaf disk assay with races 5A and 3-5A, to which powdery mildew Sf-AR most typically provides resistance. 14 plants from each family were tested for each isolate. Of those 174 CVYV resistant families, only 17 showed intermediate resistance to powdery mildew races 5A and 3-5A. These 17 families all carried a recombination event in the 82.35 and 85.09 cM region on chromosome 5, between markers between SNPmarker_9 and SNPmarker_20 (Table 3). This demonstrated that CVYV resistance on chromosome 5 is not allelic to powdery mildew resistance on chromosome 5, but instead is tightly linked. In order to fix the Sf-AR allele in these families, the lines were selfed to generate the BC1F3 generation. Further identification of polymorphic markers in the recombination region allowed further increase of the resolution on the recombination event and a slight refinement of the crossing over region (FIG. 3). The recombination event is defined by markers SNPmarker_1 at 81.50 cM, which should score positive for Hale's Best Jumbo-AR, and SNPmarker_16, which should score positive for the CVYV donor PI164323.

TABLE 3

Genotypes at markers within the 81.14 cM to 85.12 cM region of chromosome 5 correlated with phenotype.

| | Genetic positions [cM]-map v4.0.2 | | | | | | | | |
|---|---|---|---|---|---|---|---|---|---|
| Pedigree | 81.14 SNPmarker_19 | 81.50 SNPmarker_1 | 82.35 SNPmarker_9 | 85.09 SNPmarker_20 | 85.12 SNPmarker_21 | CVYV | % necrosis | PM race 5A | PM race 3-5A |
| HALES-BEST-JUMBO-AR | GG | TT | CC | AA | CC | | | 1.8 | 2 |
| PI164323 | AA | CC | TT | CC | TT | 1 | | 6.8 | |
| C2_HALES-BEST-JUMBO-AR/PI164323 | AT | CT | CT | AC | CT | | | 3.92 | 5.15 |
| C2_HALES-BEST-JUMBO-AR/PI164323_1 | AG | CT | CT | CC | TT | 1.44 | 0.36 | 3.75 | 4.5 |
| C2_HALES-BEST-JUMBO-AR/PI164323_2 | AG | CT | CT | CC | TT | 1.38 | 0.11 | 5 | 5.5 |
| C2_HALES-BEST-JUMBO-AR/PI164323_3 | AG | CT | CT | CC | TT | 1 | 0.11 | 3.25 | 5.25 |
| C2_HALES-BEST-JUMBO-AR/PI164323_4 | AG | — | CT | CC | TT | 1.53 | 0.22 | 3.5 | 4.25 |
| C2_HALES-BEST-JUMBO-AR/PI164323_5 | AG | CT | CT | CC | TT | 1 | 0.1 | 4.25 | 5.75 |
| C2_HALES-BEST-JUMBO-AR/PI164323_6 | AG | — | CT | CC | TT | 1.38 | 0.07 | 4.5 | 5 |
| C2_HALES-BEST-JUMBO-AR/PI164323_7 | AG | — | CT | CC | TT | 1 | 0.04 | 2.83 | 4 |
| C2_HALES-BEST-JUMBO-AR/PI164323_8 | AG | CT | CT | CC | TT | 1 | 0.27 | 5 | 5.86 |
| C2_HALES-BEST-JUMBO-AR/PI164323_9 | AG | CT | CT | CC | TT | 1.53 | 0.4 | 4.5 | 4.5 |
| C2_HALES-BEST-JUMBO-AR/PI164323_10 | AG | CT | CT | CC | TT | 1 | 0.1 | 5 | 4.75 |
| C2_HALES-BEST-JUMBO-AR/PI164323_11 | AG | CT | CT | CC | TT | 1 | 0.31 | 5.29 | 6 |
| C2_HALES-BEST-JUMBO-AR/PI164323_12 | AG | — | CT | CC | TT | 1 | 0.21 | 3 | 5 |
| C2_HALES-BEST-JUMBO-AR/PI164323_13 | AG | CT | CT | CC | TT | 1.53 | 0.45 | 3 | 3.75 |
| C2_HALES-BEST-JUMBO-AR/PI164323_14 | AG | CT | CT | CC | TT | 1 | 0.07 | 3.86 | 5.29 |
| C2_HALES-BEST-JUMBO-AR/PI164323_15 | AG | CC | CT | CC | TT | 1 | 0.03 | 2.75 | 3.75 |
| C2_HALES-BEST-JUMBO-AR/PI164323_16 | AG | CT | CT | CC | TT | 1 | 0.21 | 5.25 | 5.25 |
| C2_HALES-BEST-JUMBO-AR/PI164323_17 | AG | CT | CT | CC | TT | 1 | 0.28 | 4.5 | 5.25 |

Example 3

Efficacy of Coupling Event

The BC1F3 generation of the 17 lines was evaluated in further phenotypic tests to verify that the lines carried the full resistance spectrum expected for Sf-AR, aphid resistance and CVYV resistance. In addition, plants were evaluated for necrosis, which is known to be associated with CVYV resistance due to linkage drag. Lines with the best performance in phenotypic testing were used for further breeding.

Powdery Mildew and Aphid Resistance

The 17 selected BC1F3 lines were tested for powdery mildew and aphid resistance. Different PM alleles on chromosome 5 provide resistance to different PM races (Table 1). In order to ensure that the recombination event did not inadvertently change the resistance profile, plants were tested against the full spectrum of known powdery mildew races. It was expected that the plants would be resistant to the A races (2A, 3, 5A, 3-5A) and susceptible to the B races (1B, 2B, 5B, 3-5B). A leaf-test assay was performed using 3 replications of two leaves per plant (second and first leaf) of 3 two-leaf stage plants per replication (e.g. Epinat et al 1993, Kuzuya et al. 2006). The disease index was measured on a 1-9 phenotypic scale (1=resistant and 9=fully susceptible). Subsequently, the average mean disease index was calculated for each powdery mildew isolate in each line using mixed models using the statistical package JMP. Aphid resistance was tested using 2 replications with 15 plants per replication. An aphid invasion protocol was used and plants were scored based on a leaf curling assay wherein sensitive controls showed leaf curling and resistant controls did not. Resistance was scored on a phenotypic scale of 1-9, where 1 is no leaf curl and 9 is leaf curling. All lines showed resistance to aphids due to the development of leaves without leaf curling when infested with *Aphis gossypii* clone C9. This was the expected result because both Hale's-Best-Jumbo-AR and PI164323 carry resistance to *A. gossypii*. Five of the tested lines were selected for further testing based on the best powdery mildew resistance profiles.

CVYV Resistance and Necrosis

BC1F3 lines were tested for CVYV resistance and level of necrosis using two different methods. First, all 17 lines were tested in a growth chamber using the CVYV protocol as described herein. This experiment was replicated 3 times with 9 plants per replicate per line. The 5 lines selected in the powdery mildew test also had a low mean disease index for CVYV which corresponds with resistance. Only 4 of the 5 lines showed low levels of necrosis.

The 5 lines selected in the powdery mildew experiment were also evaluated for CVYV resistance and necrosis in a field setting. In this experiment, plants were exposed to white flies infected with the CVYV virus during two different seasons (spring and summer).

The experimental design for the spring experiment consisted of 3 replicates with 6 plants without necrosis symptoms for each line per replicate. In order to have enough necrosis free plants at the start of the experiment 9 seeds were sown for each line and only plants without necrosis were selected for the experiment. Each plant was scored on a 1-9 phenotypic scale (1=resistant, 9=susceptible) for CVYV resistance and necrosis. Also, the necrosis rating was determined at a plot level. In this experiment 3 of the 5 lines showed low levels of necrosis and complete CVYV resistance.

For the summer experiment, a setup with 2 replicates with 6 plants per replicate was used. The procedure was the same as for the spring experiment. However, a different necrosis scoring system was developed to distinguish between basal necrosis where the upper part of the plant was still fully green (1 n) and fully necrotic/dead plants (N). In this experiment only 2 out of 5 BC1F3 lines showed high levels of CVYV resistance and a moderate level of necrosis.

Example 4

Selection of an Event Donor for Breeding

After the phenotypic evaluation, the 5 remaining BC1F3 lines were further genotyped using a sequence capture approach. More than 30,000 primer probes were used to map the whole genome of each line. This data was used to evaluate the genetic background of each potential event donor. Particular attention was paid to the percentage of the recurrent parent in the background and the size of the introgression of wild melon line PI164323. Combining these genomic data with the phenotypic data, one line was selected as the event donor for further breeding. This line, MZZ C215-0015MO, was deposited at the ATCC under number PTA-123300. For this line the whole region with PM resistance, aphid resistance and CVYV resistance alleles was located between SNPmarker_23 and SNPmarker_21, which corresponds to a 6.1 cM region for these three traits.

The vat locus has several different alleles that provide different versions of powdery mildew resistance. In order to demonstrate the generality of the recombination region described herein for coupling of other powdery mildew resistance alleles with CVYV, plants comprising Sf-VB coupled to CVYV were generated. Analysis of recombinants showed that recombination occurred between SNPmarker_9 and SNPmarker_22. As with the Sf-AR-CVYV coupling event, a breeding event was created that was flanked by SNPmarker_23 and SNPmarker_21. The result is a donor line that allows breeders to easily introgress the cis-linked combination of Sf-VB based powdery mildew resistance and CVYV resistance into other susceptible melon lines. This donor line, MZZ-C216-0017MO has been deposited at the ATCC under number PTA-124003. It was demonstrated that recombination in the same region as the Sf-AR-CVYV event leads to plants that are powdery mildew resistant, aphid resistant, and CVYV resistant. This suggests that any powdery mildew allele that is allelic to the vat locus can be coupled to CVYV when crossing over occurs between markers SNPmarker_1 at 81.50 cM, which should score positive for the PM donor, and SNPmarker_21, which should score positive for the CVYV donor PI164323. Recombination between any combination of markers as indicated in FIG. 3 will lead to coupling of PM resistance to CVYV resistance in cis configuration as long as a marker polymorphic between the PM donor and recipient germplasm is used and a marker polymorphic between the CVYV donor PI164323 and the recipient germplasm is used. This can be any marker located between SNPmarker_23 and SNPmarker_21, for example any combination of markers indicated in FIG. 3. For instance, SNPmarker_9 scores positive for the PM donor and SNPmarker_22 scores positive for the CVYV donor PI164323, or SNPmarker_5 (SEQ ID NO: 5) scores positive for the PM donor and SNPmarker_6 (SEQ ID NO: 6) scores positive for the CVYV resistance donor PI164323, etc.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A melon plant of a cultivated melon plant variety comprising a chromosomal segment that comprises a first allele conferring Powdery Mildew resistance at marker locus SNPmarker_1 and a second allele conferring resistance to Cucumber Vein Yellowing Virus (CVYV) at marker locus SNPmarker_22, wherein said first allele and said second allele are configured in cis linkage on chromosome 5, wherein said first allele is present in the genome of a plant of Hale's Best Jumbo-AR, a plant of melon line MZZ C215-0015MO or a plant of melon line MZZ-C216-0017MO, a representative deposit of seed of said line MZZ C215-0015MO and said line MZZ-C216-0017MO having been deposited under ATCC Accession Nos. PTA-124003 and PTA-123300, respectively; and wherein said second allele is present in the genome of a plant of P1164323.

2. The melon plant of claim 1, wherein said chromosomal segment further comprises a third allele conferring resistance to *Aphis gossypii*.

3. The melon plant of claim 1, wherein said chromosomal segment is flanked by marker loci SNPmarker_23 and SNPmarker_21 on chromosome 5.

4. The melon plant of claim 1, wherein said Powdery Mildew resistance allele is detected at marker locus SNPmarker_1 and said CVYV allele is detected at marker locus SNPmarker_16 on chromosome 5.

5. The melon plant of claim 1, wherein said Powdery Mildew allele is detected at marker locus SNPmarker_9 and said CVYV allele is detected at marker locus SNPmarker_22 on chromosome 5.

6. The melon plant of claim 1, wherein said plant comprises an introgressed chromosomal segment from a Powdery Mildew resistant parent plant at a genomic locus flanked by marker locus SNPmarker_1 and marker locus SNPmarker_23 on chromosome 5.

7. The melon plant of claim 6, wherein said plant comprises an introgressed chromosomal segment from Hale's Best Jumbo-AR at a locus genetically linked to marker locus SNPmarker_1 on chromosome 5.

8. The melon plant of claim 1, wherein said plant comprises an introgressed chromosomal segment from a CVYV resistant parent plant at a genomic region flanked by marker locus SNPmarker_16 and marker locus SNPmarker_21 on chromosome 5.

9. The melon plant of claim 8, wherein said plant comprises an introgressed chromosomal segment from PI164323 at a locus genetically linked to marker locus SNPmarker_16 on chromosome 5.

10. The melon plant of claim 1, wherein the plant comprises an introgressed chromosomal segment from a Powdery Mildew resistant parent plant at marker locus SNPmarker_1 on chromosome 5 and an introgressed chromosomal segment from a CVYV resistant parent plant at marker locus SNPmarker_16 on chromosome 5.

11. The melon plant of claim 1, wherein the plant comprises an introgressed chromosomal segment from a Powdery Mildew resistant parent plant at marker locus SNPmarker_1 on chromosome 5 and an introgressed chromosomal segment from a CVYV resistant parent plant at marker locus SNPmarker_22 on chromosome 5.

12. The melon plant of claim 10, wherein said plant comprises an introgressed chromosomal segment from Hale's Best Jumbo-AR at a locus genetically linked to marker locus SNPmarker_1 on chromosome 5 and an introgressed chromosomal segment from PI164323 at a locus genetically linked to marker locus SNPmarker_16 on chromosome 5.

13. The melon plant of claim 1, wherein a representative sample of seed comprising said chromosomal segment has been deposited under Accession No. PTA-123300 or under Accession No. PTA-124003.

14. A plant part of the melon plant of claim 1.

15. The plant part of claim 14, wherein the plant part is a cell, a seed, a root, a stem, a leaf, a fruit, a flower, or pollen.

16. A method of selecting a melon plant exhibiting resistance to Powdery Mildew and CVYV, said method comprising:
   a) crossing the melon plant of claim 1 with itself or with a second melon plant of a different genotype to produce one or more progeny plants; and
   b) selecting a progeny plant comprising said chromosomal segment.

17. The method of claim 16, wherein selecting said progeny plant comprises marker-assisted selection.

18. The method of claim 17, wherein said marker-assisted selection comprises detecting at least one allele at a genomic locus flanked by marker loci SNPmarker_19 and SNPmarker_21.

19. The method of claim 18, wherein said marker-assisted selection comprises detecting at least one allele at a genomic locus flanked by marker loci SNPmarker_1 and SNPmarker_16.

20. The method of claim 17, wherein said marker-assisted selection comprises detecting at least one allele at a locus genetically linked to a marker locus selected from the group consisting of: SNPmarker_1, SNPmarker_2, SNPmarker_3, SNPmarker_4, SNPmarker_5, SNPmarker_6, SNPmarker_7, SNPmarker_8, SNPmarker_9, SNPmarker_10, SNPmarker_11, SNPmarker_12, SNPmarker_13, SNPmarker_14, SNPmarker_15, SNPmarker_16, SNPmarker_17, SNPmarker_18, SNPmarker_19, SNPmarker_20, SNPmarker_21, SNPmarker_22, and SNPmarker_23.

21. The method of claim 20, wherein said marker-assisted selection comprises detecting at least one allele at a locus genetically linked to a marker locus selected from the group consisting of: SNPmarker_1 and SNPmarker_21.

22. The method of claim 16, wherein said progeny plant is an F2-F6 progeny plant.

23. The method of claim 16, wherein producing said progeny plant comprises backcrossing.

24. The method of claim 23, wherein backcrossing comprises from 2-7 generations of backcrossing.

25. A plant produced by the method of claim 16.

26. A part of the plant of claim 25, selected from the group consisting of a cell, a seed, a root, a stem, a leaf, a fruit, a flower, and pollen.

* * * * *